(12) United States Patent
Park

(10) Patent No.: US 6,239,707 B1
(45) Date of Patent: May 29, 2001

(54) DRIVER CONDITION MONITORING APPARATUS

(76) Inventor: Won-Hee Park, No. 11-801, Imkwang Apartment, 1011-1, Bangbea-3 Dong, Socho Ku, Seoul 137-755 (KR)

( * ) Notice: Subject to any disclaimer, the term of this patent is extended or adjusted under 35 U.S.C. 154(b) by 0 days.

(21) Appl. No.: 09/547,266

(22) Filed: Apr. 11, 2000

(30) Foreign Application Priority Data

Feb. 22, 2000 (KR) .................................................. 00-8514
Mar. 16, 2000 (KR) ................................................. 00-13386

(51) Int. Cl.⁷ .................................................. G08B 23/00
(52) U.S. Cl. ........................ 340/576; 340/573.1; 600/301
(58) Field of Search ..................................... 340/576, 575, 340/573.1, 465, 539; 128/902, 903; 600/300, 301

(56) References Cited

U.S. PATENT DOCUMENTS

| | | | |
|---|---|---|---|
| 4,706,072 | * 11/1987 | Ikeyama | 340/576 |
| 5,574,641 | * 11/1996 | Kawakami et al. | 340/576 |
| 5,783,997 | * 7/1998 | Saitoh et al. | 340/576 |
| 5,813,989 | * 9/1998 | Saitoh et al. | 340/576 |
| 5,917,415 | * 6/1999 | Atlas | 340/575 |
| 6,104,296 | * 8/2000 | Yasushi et al. | 340/576 |

* cited by examiner

*Primary Examiner*—Nina Tong
(74) *Attorney, Agent, or Firm*—Levine & Mandelbaum

(57) ABSTRACT

A driver condition monitoring apparatus comprising a pulse sensor 1 installed in a steering wheel of a transportation device for sensing a pulse signal from the palm or fingers of either or both of the left and right hands of a driver, an amplifier 2 for amplifying the pulse signal sensed by the pulse sensor 1 and removing a noise component therefrom, a keypad 4 including a plurality of keys for inputting information about the driver, a data storage unit 5 for storing the driver information inputted through the keypad 4 and reference data produced when the driver selects a reference data input mode in his normal healthy condition, a controller 3 for comparing pulse signals sensed by the pulse sensor 1 before, after and while driving, respectively with the reference data stored in the data storage unit 5, analyzing each of the compared results, judging the current condition of the driver from the analyzed result and visually and aurally informing the driver of the judged result respectively through a display 8 and speaker 7, an audio processor 6 for converting a specified one of various voice data stored in the data storage unit 5 into an audio signal, amplifying the converted audio signal and outputting it to the speaker 7, and a power supply 9 for supplying an operating voltage to the driver condition monitoring apparatus.

11 Claims, 4 Drawing Sheets

DRIVER CONDITION MONITORING APPARATUS

TECHNICAL FIELD

The present invention relates in general to an apparatus for sensing a pulse signal from the palm or fingers of either or both of the left and right hands of a driver through a pulse sensor on a steering wheel of a transportation device such as an airplane, ship, vehicle, two-wheeled vehicle or heavy equipment and monitoring the condition of the driver in accordance with the sensed result, and more particularly to a driver condition monitoring apparatus for sensing a pulse signal from the palm or fingers of either or both of the left and right hands of a driver through a pulse sensor on a steering wheel of a transportation device, measuring the condition of the driver while driving, such as sleepiness, fatigue, physical abnormality, etc., in accordance with the sensed result and visually and aurally informing the driver of the measured result, thereby preventing accidents while driving.

BACKGROUND ART

Generally, operators and drivers (referred to hereinafter only as drivers) for an airplane, ship, vehicle, two-wheeled vehicle, heavy equipment, etc. (referred to hereinafter only as transportation devices) must often inevitably drive the transportation devices even under the condition that they are tired or overworked, because their driving schedules are not fixed. For this reason, the drivers may encounter the danger of serious accidents due to sleepy driving resulting from their fatigue.

On the other hand, the above drivers for the transportation devices usually make self-diagnoses of their bodies on the basis of symptoms and habits appearing on their bodies to determine whether they are currently overworked or tired. When the drivers determine that they are tired, they drive the transportation devices after sleeping or taking a reset. However, such self-diagnoses of the drivers are unscientific and, when certain symptoms instantaneously appear while driving, the drivers must judge the current conditions by themselves. As a result, it is the reality that the drivers for the transportation devices are always exposed to the danger of serious accidents.

DISCLOSURE OF THE INVENTION

Therefore, the present invention has been made in view of the above problems, and it is an object of the present invention to provide a driver condition monitoring apparatus or sensing a pulse signal from the palm or fingers of either or both of the left and right hands of a driver through a pulse sensor on a steering wheel of a transportation device in a normal healthy condition of the driver, storing the sensed result as reference data in a data storage unit, sensing a pulse signal from the palm or fingers of either or both of the left and right hands of the driver through the pulse sensor on the steering wheel of the transportation device while driving, measuring a variation of the sensed pulse signal resulting from overwork, sleepiness, excitement, vehicle overtaking, excessive speeding, etc. of the driver, comparing the measured result with the reference data stored in the data storage unit and, when a difference therebetween is above or below a threshold value, calling his attention to the current condition or cautioning him against it in a picture or voice, thereby guiding the driver to adequately cope with the current condition to prevent accidents while driving.

In accordance with the present invention, the above and other objects can be accomplished by a provision of a driver condition monitoring apparatus for checking a physical condition of a driver driving any one of transportation devices including an airplane, ship, vehicle, two-wheeled vehicle and heavy equipment and informing the driver of the checked physical condition, comprising a pulse sensor installed in a steering wheel of a given one of the transportation devices for sensing a pulse signal (electrocardiogram signal) from the palm or fingers of either or both of the left and right hands of the driver; an amplifier for amplifying the pulse signal sensed by the pulse sensor and removing a noise component therefrom; a keypad including a plurality of keys for inputting information about the driver; a data storage unit for storing the driver information inputted through the keypad from the driver and reference data based on a pulse signal from the palm or fingers of either or both of the left and right hands of the driver, sensed by the pulse sensor when the driver selects a reference data input mode in his normal healthy condition; a controller for comparing pulse signals from the palm or fingers of either or both of the left and right hands of the driver, sensed by the pulse sensor before, after and while driving, respectively with the reference data stored in the data storage unit, analyzing each of the compared results, judging the current condition of the driver from the analyzed result and visually and aurally informing the driver of the judged result respectively through a display and speaker; an audio processor responsive to a first control signal from the controller for converting a specified one of various voice data stored in the data storage unit into an audio signal, amplifying the converted audio signal and outputting it to the speaker; the display responsive to a second control signal from the controller for displaying the measured condition of the driver in a numerical value or picture; and a power supply for supplying an operating voltage to the driver condition monitoring apparatus using a self power source of the given transportation device.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

In accordance with the present invention, a driver condition monitoring apparatus is provided to sense a pulse signal from the palm or fingers of either or both of the left and right hands of a driver through a pulse sensor on a steering wheel of a transportation device in a normal healthy condition of the driver, store the sensed result as reference data in a data storage unit, sense a pulse signal from the palm or fingers of either or both of the left and right hands of the driver through the pulse sensor on the steering wheel of the transportation device while driving, measure a variation of the sensed pulse signal resulting from sleepiness, fatigue, physical abnormality, etc. of the driver, compare the measured result with the reference data stored in the data storage unit, analyze the compared result and monitor the condition of the driver in accordance with the analyzed result.

Figure 1:
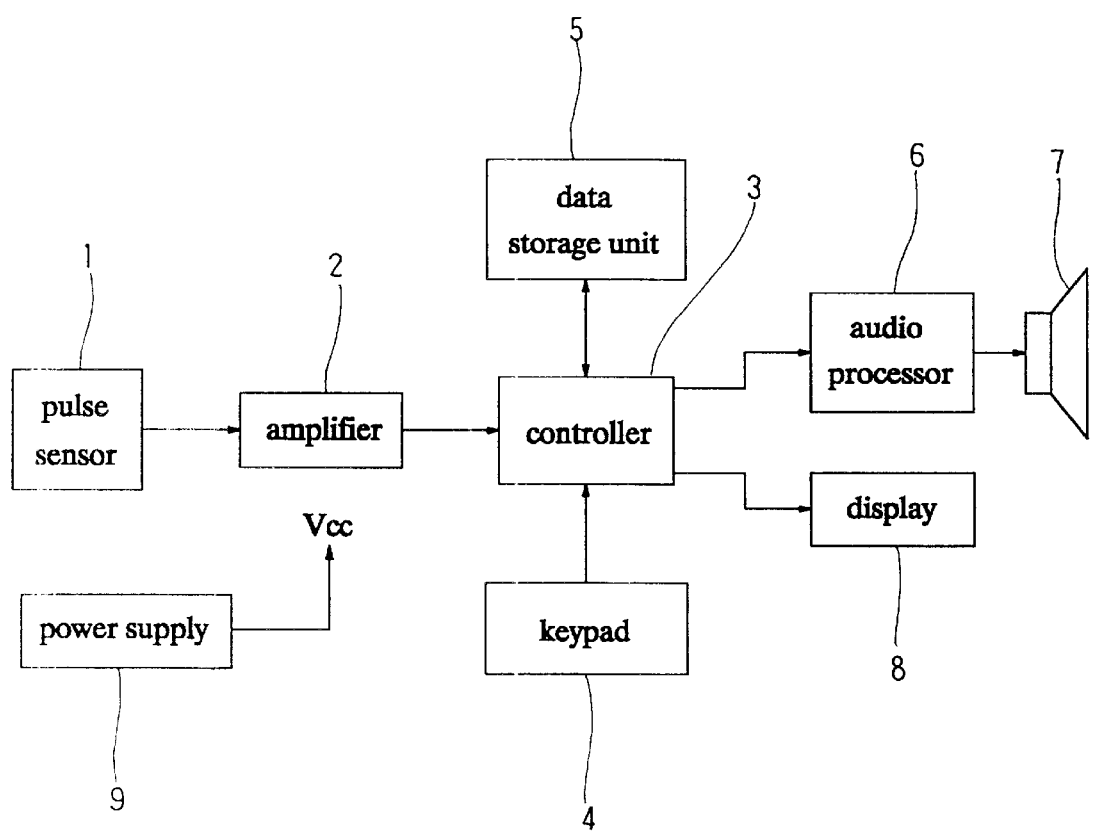
FIG. 1 is a schematic block diagram of the construction of a driver condition monitoring apparatus in accordance with an embodiment of the present invention.
Figure 2:
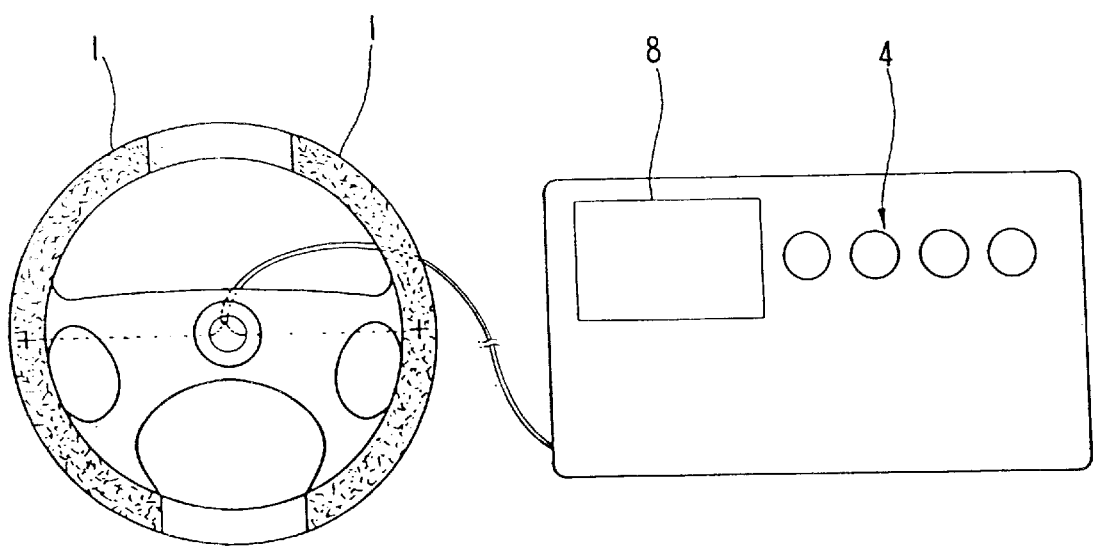
FIG. 2 is a view showing the configuration of a pulse sensor electrode on a steering wheel itself of a transportation device in accordance with the embodiment of the present invention.

FIG. 1 is a schematic block diagram of the construction of a driver condition monitoring apparatus in accordance with an embodiment of the present invention, and FIG. 2 is a view showing the configuration of a pulse sensor electrode on a steering wheel itself of a transportation device in accordance with the embodiment of the present invention.

In FIGS. 1 and 2, the reference numeral 1 denotes a pulse sensor contained within the whole of the steering wheel of the transportation device or attached to the entire surface of the steering wheel for coming into contact with the skin of the palm or fingers of either or both of the left and right hands of a driver. The pulse sensor 1 is preferably made of a material conductible and contactable with the skin of the driver, and it functions to sense a pulse signal generated with the beating of the driver's heart from the palm or fingers of either or both of the left and right hands of the driver using the principle of an electrocardiogram. The reference numeral 2 denotes an amplifier for amplifying the pulse signal sensed by the pulse sensor 1 and removing a noise component therefrom.

The reference numeral 3 denotes a controller for comparing a pulse signal from the palm or fingers of either or both of the left and right hands of the driver, sensed by the pulse sensor 1, with reference data of the driver stored in a data storage unit 5, analyzing the compared result, judging the current condition of the driver from the analyzed result and displaying the judged result visually through a display 8 or outputting it as voice information through a speaker 7.

The reference numeral 4 denotes a keypad including a power switch, a mode selection key and a plurality of keys for measurement of body fat of the driver, not shown. The body fat measurement keys may be, for example, a stature key, weight key, age key, sex key, etc. The data storage unit 5 acts to store information about the driver such as the stature, weight, age, sex, etc. of the driver, inputted through the keypad 4 from the driver. Further, the data storage unit 5 stores reference data based on a pulse signal from the palm or fingers of either or both of the left and right hands of the driver, sensed by the pulse sensor 1 when the driver selects a reference data input mode in his normal healthy condition.

The reference numeral 6 denotes an audio processor responsive to a control signal from the controller 3 for converting a specified one of various voice data stored in the data storage unit 5 into an audio signal, amplifying the converted audio signal and outputting it to the speaker 7. The speaker 7 outputs the audio signal from the audio processor 6 externally as an audible voice. The display 8 is installed in a fascia board, the steering wheel or any position of the transportation device readily viewable by the driver to display the condition of the driver in a numerical value or picture based on a pulse signal from the palm or fingers of either or both of the left and right hands of the driver, sensed by the pulse sensor 1. The reference numeral 9 denotes a power supply for supplying an operating voltage Vcc to the driver condition monitoring apparatus using a self power source of the transportation device.

Now, a detailed description will be given of the operation of the driver condition monitoring apparatus with the above-mentioned construction in accordance with the preferred embodiment of the present invention.

First, if the driver for the transportation device selects the reference data input mode using the mode selection key on the keypad 4 under the condition that he obtains a sufficient rest, then a pulse signal from the palm or fingers of either or both of the left and right hands of the driver is measured through the pulse sensor 1 on the steering wheel of the transportation device and set as reference data of the driver. That is, if the driver selects the reference data input mode and brings the palm or fingers of either or both of his left and right hands into contact with the pulse sensor 1, then a loop is formed through either or both of the palms or fingers and the pulse sensor 1, thereby causing the pulse sensor 1 to sense a pulse signal generated with the beating of the driver's heart using the principle of an electrocardiogram.

Subsequently, the amplifier 2 amplifies the pulse signal sensed by the pulse sensor 1 to a predetermined level and removes a noise component therefrom. The controller 3 stores the pulse signal amplified and noise-removed by the amplifier 2 as reference data in the data storage unit 5. Further, the controller 3 controls the audio processor 6 to output a voice information message, for example, "The reference data has been inputted" through the speaker 7 and controls the display 8 to display the measured reference data.

Thereafter, if the driver drives the transportation device or turns on the power switch under the condition that the reference data is stored in the data storage unit 5 in the above manner, then the driver condition monitoring apparatus is operated and the pulse sensor 1 therein senses a pulse signal from the palm or fingers of either or both of the left and right hands of the driver. The controller 3 compares the pulse signal sensed by the pulse sensor 1 with the reference data stored in the data storage unit 5 and analyzes the compared result. At this time, in the case where a difference between the sensed pulse signal and the stored reference data is above or below a threshold value, namely, beyond an allowable error range, for example, ±5%, the controller 3 controls the audio processor 6 to output a voice information message, for example, "Your pulse rate is high. You should take a rest" through the speaker 7 and controls the display 8 to display the measured data in a numerical value or picture in a flickering manner. Also, in the case where the difference between the sensed pulse signal and the stored reference data is above or below a greater threshold value, namely, beyond a wider allowable error range, for example, ±10%, the controller 3 controls the audio processor 6 to output a voice information message, for example, "Your pulse rate is dangerously high. You should take a rest for a moment" through the speaker 7 and controls the display 8 to display the measured data in a numerical value or picture in the flickering manner.

On the other hand, the pulse measurement interval can be automatically corrected or set to a fixed time according to the operation of the keypad 4 by the driver. For example, the driver may continuously move the palm or fingers of either or both of his left and right hands on the pulse sensor 1 on the steering wheel to such a degree that there is not enough time for pulse sensing. In this case, even though the pulse measurement interval is set to, for example, 60 seconds, the controller 3 sequentially reduces the pulse measurement interval from 60 seconds to 30, 10 and 3 seconds until the pulse sensor 1 instantaneously senses a pulse signal from the palm or fingers of either or both of the left and right hands of the driver. In the case where the driver stably brings his palm or fingers into contact with the pulse sensor 1 on the steering wheel for 60 seconds or more, the controller 3 returns the pulse measurement interval to the original time, or 60 seconds.

Preferably, the controller 3 may determine whether the driver has arrhythmia, on the basis of a plurality of pulse signals from the palm or fingers of either or both of the left and right hands of the driver, sensed by the pulse sensor 1 on the steering wheel of the transportation device. For example, in the case where pulse signals, sensed a number of times at an interval of a predetermined period of time, are irregular in interval and strength, the controller 3 determines that the driver has the arrhythmia.

Upon determining that the driver has the arrhythmia, the controller 3 controls the audio processor 6 to output a voice information message, for example, "You have arrhythmia" through the speaker 7 and controls the display 8 to display the presence of arrhythmia in the flickering manner, thereby guiding the driver to receive medical treatment from a medical institution.

On the other hand, if the driver selects a body fat measurement mode using the mode selection key on the keypad 4 and brings the palms of his left and right hands into contact with the pulse sensor 1 on the steering wheel for a predetermined period of time, for example, 10 seconds or more, then the controller 3 measures body fat of the driver on the basis of the driver information stored in the data storage unit 5, such as the stature, weight, age, sex, etc. of the driver, and displays the measured result through the display 8 in a numerical value.

Figure 3:
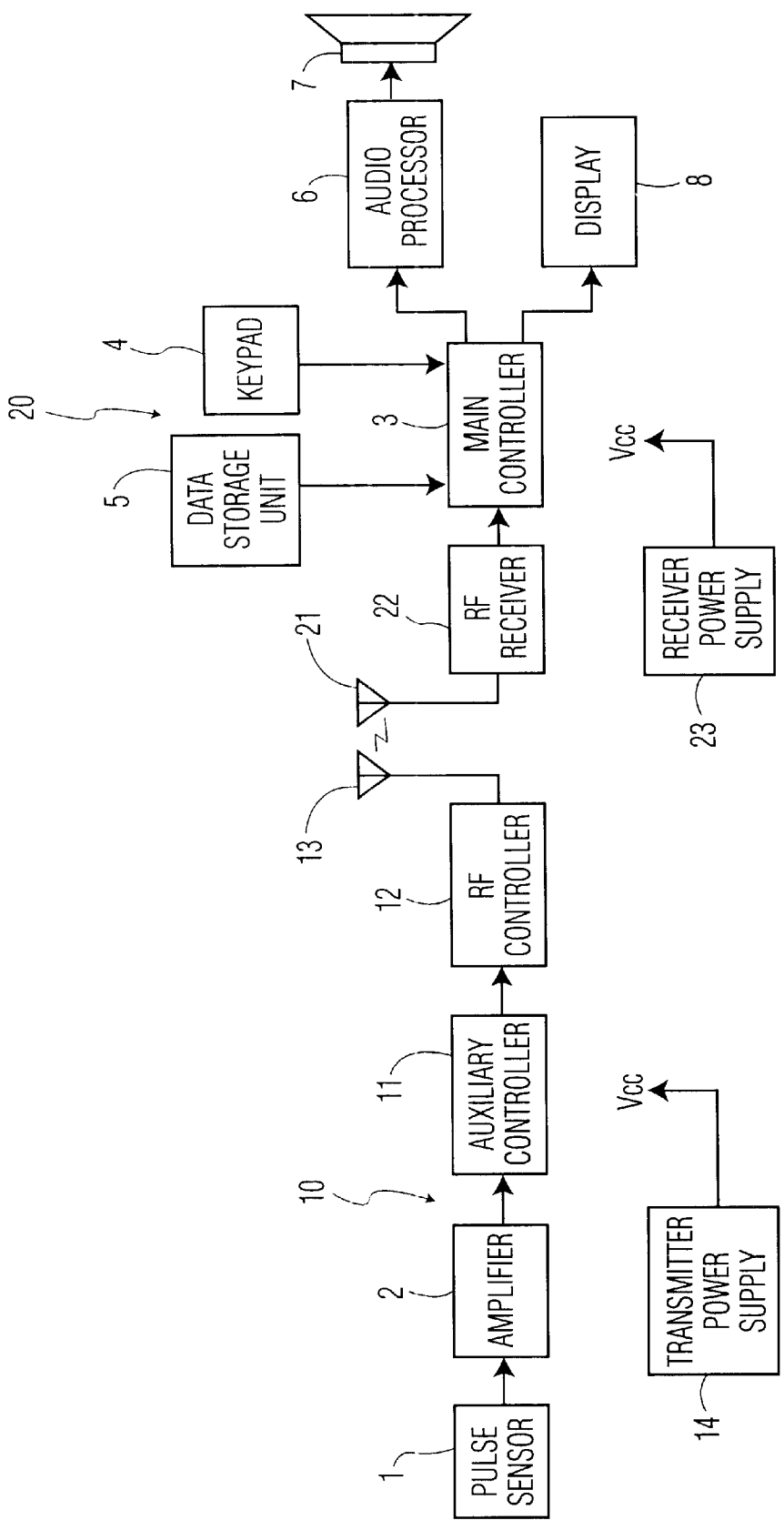
FIG. 3 is a schematic block diagram of the construction of a driver condition monitoring apparatus in accordance with an alternative embodiment of the present invention.
Figure 4:
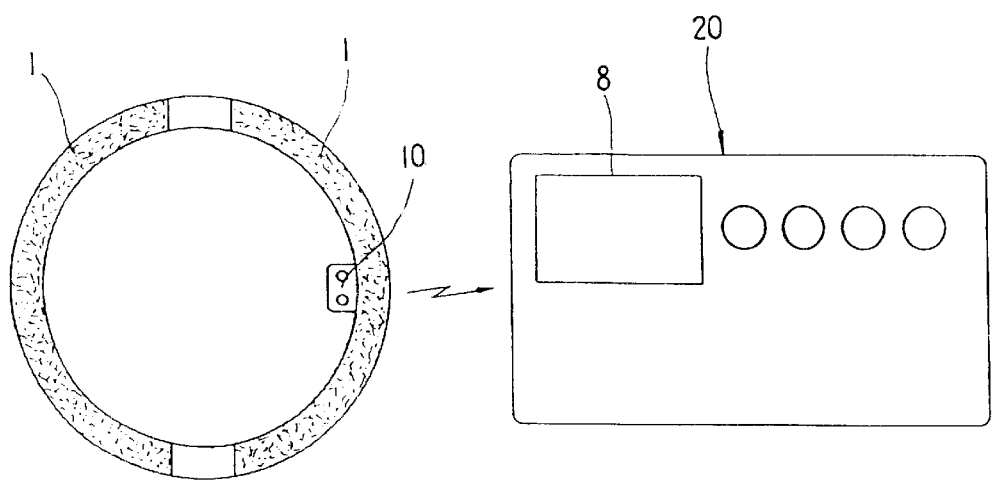
FIG. 4 is a view showing the configuration of a pulse sensor electrode on a steering wheel cover of a transportation device in accordance with the second embodiment of the present invention.
Figure 5:
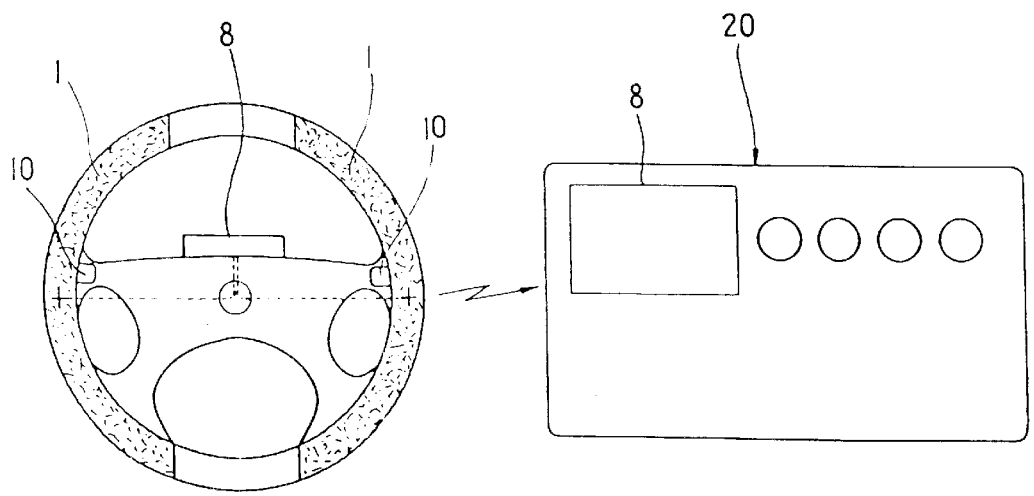
FIG. 5 is a view showing the configuration of a receiver and display on a steering wheel of the transportation device in accordance with the second embodiment of the present invention.

FIG. 3 is a schematic block diagram of the construction of a driver condition monitoring apparatus in accordance with an alternative embodiment of the present invention, FIG. 4 is a view showing the configuration of a pulse sensor electrode on a steering wheel cover of a transportation device in accordance with the second embodiment of the present invention, and FIG. 5 is a view showing the configuration of a receiver and display on a steering wheel of the transportation device in accordance with the second embodiment of the present invention. Some parts in the second embodiment are substantially the same in construction and operation as those in the first embodiment. Therefore, in the second embodiment, the same parts as those in the first embodiment are denoted by the same reference numerals and a detailed description thereof will thus be omitted.

As shown in FIGS. 3 to 5, the driver condition monitoring apparatus comprises a transmitter module 10 attached to the steering wheel of the transportation device. The transmitter module 10 includes a pulse sensor 1 attached to the steering wheel for sensing a pulse signal from the palm or fingers of either or both of the left and right hands of a driver, an amplifier 2 for amplifying the pulse signal sensed by the pulse sensor 1 and removing a noise component therefrom, an auxiliary controller 11 for converting an analog pulse signal from the amplifier 2 into a digital pulse signal, a radio frequency (RF) transmitter 12 for modulating the digital pulse signal from the auxiliary controller 11 into an RF signal, amplifying the modulated RF signal and transmitting it by radio through a transmitting antenna 13, and a transmitter power supply 14 for supplying an operating voltage Vcc to the transmitter module 10 using a self power source of the transportation device or a rechargeable or dry cell battery.

The driver condition monitoring apparatus further comprises a receiver module 20 installed in a fascia board, the steering wheel or any position of the transportation device readily viewable by the driver. The receiver module 20 includes an RF receiver 22 for receiving the RF signal from the RF transmitter 12 in the transmitter module 10 through a receiving antenna 21, demodulating it into the original pulse signal (electrocardiogram signal) and amplifying the demodulated pulse signal, a keypad 4 including a power switch, a mode selection key and a plurality of other keys, and a data storage unit 5 for storing driver information inputted through the keypad 4 from the driver and reference data measured in a reference data input mode selected by the driver. The receiver module 20 further includes a main controller 3 for comparing an output pulse signal from the RF receiver 22 with the reference data stored in the data storage unit 5, analyzing the compared result, judging the current condition of the driver from the analyzed result and displaying the judged result visually through a display 8 or outputting it as voice information through a speaker 7, an audio processor 6 responsive to a control signal from the main controller 3 for converting a specified one of various voice data stored in the data storage unit 5 into an audio signal, amplifying the converted audio signal and outputting it to the speaker 7, and a receiver power supply 14 for supplying the operating voltage Vcc to the receiver module 20 using the self power source of the transportation device or the rechargeable or dry cell battery.

In accordance with the second embodiment of the present invention, the transmitter module 10 of the driver condition monitoring apparatus has a circular steering wheel cover shape, within the whole of which is contained the pulse sensor 1. Therefore, the transmitter module 10 is installable in a transportation device with a circular steering wheel to sense a driver's pulse signal in the same manner as the first embodiment.

Alternatively, the transmitter module 10 of the driver condition monitoring apparatus may have, for example, a rectangular shape to be attachable to a bar-shaped steering wheel, not shown. Further, the transmitter module 10 may have a variety of shapes such as circular, square and rectangular shapes so far as it is detachable from a given steering wheel. For example, the transmitter module 10 may be attached to a steering wheel or shift lever grip of a transportation device or directly to the skin of a driver to sense a pulse signal from the palm or fingers of either or both of the left and right hands of the driver, modulate the sensed pulse signal into an RF signal and transmit the modulated RF signal by radio.

The receiver module 20 of the driver condition monitoring apparatus demodulates the RF signal from the transmitter module 10 into the original pulse signal and calls the driver's attention to the current condition through the display 8 or speaker 7.

Therefore, the present driver condition monitoring apparatus is capable of checking the current condition of the driver in response to a pulse signal from the palm or fingers of either or both of the left and right hands of the driver, sensed through the pulse sensor on the steering wheel, and calling his attention to the current condition or cautioning him against it in a voice, buzzer, numerical value or picture, thereby guiding the driver to adequately cope with the current condition to prevent accidents while driving.

INDUSTRIAL APPLICABILITY

As apparent from the above description, the present invention provides a driver condition monitoring apparatus which senses a pulse signal from the palm or fingers of either or both of the left and right hands of a driver through a pulse sensor on a steering wheel of a transportation device in a normal healthy condition of the driver, stores the sensed result as reference data in a data storage unit, senses a pulse signal from the palm or fingers of either or both of the left and right hands of the driver through the pulse sensor on the steering wheel of the transportation device while driving, measures a physical variation of the driver in response to the sensed pulse signal, compares the measured result with the reference data stored in the data storage unit, analyzes the compared result and visually and aurally informs the driver of the analyzed result, thereby guiding the driver to adequately cope with the current condition to prevent serious accidents due to sleepy driving, etc.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A driver condition monitoring apparatus for checking a physical condition of a driver driving any one of transportation devices including an airplane, ship, vehicle, two-wheeled vehicle and heavy equipment and informing the driver of the checked physical condition, comprising:

a pulse sensor installed in a steering wheel of a given one of said transportation devices for sensing a pulse signal (electrocardiogram signal) from the palm or fingers of either or both of the left and right hands of said driver;

an amplifier for amplifying the pulse signal sensed by said pulse sensor and removing a noise component therefrom;

a keypad including a plurality of keys for inputting information about said driver;

a data storage unit for storing said driver information inputted through said keypad from said driver and reference data based on a pulse signal from the palm or fingers of either or both of the left and right hands of said driver, sensed by said pulse sensor when said driver selects a reference data input mode in his normal healthy condition;

a controller for comparing pulse signals from the palm or fingers of either or both of the left and right hands of said driver, sensed by said pulse sensor before, after and while driving, respectively with said reference data stored in said data storage unit, analyzing each of the compared results, judging the current condition of said driver from the analyzed result and visually and aurally informing said driver of the judged result respectively through a display and speaker;

an audio processor responsive to a first control signal from said controller for converting a specified one of various voice data stored in said data storage unit into an audio signal, amplifying the converted audio signal and outputting it to said speaker;

said display responsive to a second control signal from said controller for displaying the measured condition of said driver in a numerical value or picture; and a power supply for supplying an operating voltage to said driver condition monitoring apparatus using a self power source of said given transportation device.

2. The driver condition monitoring apparatus as set forth in claim 1, wherein said pulse sensor is contained within both sides of said steering wheel of said given transportation device in a manufacturing process of said given transportation device, said pulse sensor being made of a material conductible and contactable with the skin of the palm or fingers of either or both of the left and right hands of said driver.

3. The driver condition monitoring apparatus as set forth in claim 1, wherein said display is installed in a fascia board of said given transportation device.

4. The driver condition monitoring apparatus as set forth in claim 1, wherein said display is installed in a predetermined portion of said steering wheel of said given transportation device.

5. The driver condition monitoring apparatus as set forth in claim 1, wherein said controller is adapted to, if said driver brings the palms or fingers of his left and right hands into contact with said pulse sensor on said steering wheel for a predetermined period of time, measure body fat of said driver on the basis of said driver information stored in said data storage unit and inform said driver of the measured result in a numerical value and voice respectively through said display and speaker, said driver information including a stature, weight, age and sex of said driver.

6. The driver condition monitoring apparatus as set forth in claim 1, wherein said controller is adapted to display a graphic of an electrocardiogram through said display if said driver selects an electrocardiogram mode using a mode selection key on said keypad and brings the palms or fingers of his left and right hands into contact with said pulse sensor on said steering wheel for a predetermined period of time.

7. The driver condition monitoring apparatus as set forth in claim 1, wherein said pulse sensor includes its terminals contained respectively within a plurality of grips installed in said given transportation device.

8. A driver condition monitoring apparatus for checking a physical condition of a driver driving any one of transportation devices including an airplane, ship, vehicle, two-wheeled vehicle and heavy equipment and informing the driver of the checked physical condition, comprising:

a transmitter module including a pulse sensor installed in a steering wheel of a given one of said transportation devices for sensing a pulse signal (electrocardiogram signal) from the palm or fingers of either or both of the left and right hands of said driver, an amplifier for amplifying the pulse signal sensed by said pulse sensor and removing a noise component therefrom, an auxiliary controller for converting an analog pulse signal from said amplifier into a digital pulse signal, a radio frequency transmitter for modulating the digital pulse signal from said auxiliary controller into a radio frequency signal, amplifying the modulated radio frequency signal and transmitting it by radio through a transmitting antenna, and a transmitter power supply for supplying an operating voltage to said transmitter module using a self power source of said given transportation device or a rechargeable battery; and a receiver module including a radio frequency receiver for receiving the radio frequency signal from said radio frequency transmitter in said transmitter module through a receiving antenna, demodulating it into the original pulse signal and amplifying the demodulated pulse signal, a keypad including a plurality of keys for inputting information about said driver, a data storage unit for storing said driver information inputted through said keypad from said driver and reference data based on a pulse signal from the palm or fingers of either or both of the left and right hands of said driver, sensed by said pulse sensor when said driver selects a reference data input mode in his normal healthy condition, a main controller for comparing pulse signals from the palm or fingers of either or both of the left and right hands of said driver, sensed by said pulse sensor before, after and while driving, respectively with said reference data stored in said data storage unit, analyzing each of the compared results, judging the current condition of said driver from the analyzed result and visually and aurally informing said driver of the judged result respectively through a display and speaker, an audio processor responsive to a first control signal from said main controller for converting a specified one of various voice data stored in said data storage unit into an audio signal, amplifying the converted audio signal and outputting it to said speaker, said display responsive to a second control signal from said main controller for displaying the measured condition of said driver in a numerical value, and a receiver power supply for supplying said operating voltage to said receiver module using the self power source of said given transportation device or the rechargeable battery.

9. The driver condition monitoring apparatus as set forth in claim 8, wherein said steering wheel of said given transportation device has a circular shape and said transmitter module has a steering wheel cover shape to be installable in said circular steering wheel, said pulse sensor being attached to both sides of said steering wheel cover shape.

10. The driver condition monitoring apparatus as set forth in claim 8, wherein said transmitter module is detachably attached to said steering wheel or a plurality of grips of said given transportation device or directly to the skin of said driver to sense a pulse signal from the palm or fingers of either or both of the left and right hands of said driver.

11. The driver condition monitoring apparatus as set forth in claim 8, wherein said receiver module is installed in a predetermined portion of a fascia board of said given transportation device in such a manner it can readily be operated and viewed by said driver while driving.

* * * * *